(12) United States Patent
Mansour et al.

(10) Patent No.: US 7,930,015 B2
(45) Date of Patent: Apr. 19, 2011

(54) METHODS AND SENSORS FOR MONITORING INTERNAL TISSUE CONDITIONS

(76) Inventors: Hebah Noshy Mansour, La Mirada, CA (US); Ramez Emile Necola Shehada, La Mirada, CA (US)

( * ) Notice: Subject to any disclaimer, the term of this patent is extended or adjusted under 35 U.S.C. 154(b) by 963 days.

(21) Appl. No.: 11/354,346

(22) Filed: Feb. 14, 2006

(65) Prior Publication Data
US 2006/0200012 A1 Sep. 7, 2006

Related U.S. Application Data

(60) Provisional application No. 60/652,939, filed on Feb. 14, 2005.

(51) Int. Cl.
*A61M 1/00* (2006.01)
(52) U.S. Cl. .......... 600/476; 600/342; 600/478
(58) Field of Classification Search .......... 600/317, 600/342, 488, 310, 320, 323, 361, 363, 407, 600/476, 478; 604/317, 504
See application file for complete search history.

(56) References Cited

U.S. PATENT DOCUMENTS

| | | | |
|---|---|---|---|
| 4,321,930 A * | 3/1982 | Jobsis et al. .......... 600/344 |
| 5,571,099 A * | 11/1996 | Purcell et al. .......... 606/17 |
| 5,769,791 A | 6/1998 | Benaron |
| 5,785,658 A * | 7/1998 | Benaron et al. .......... 600/473 |
| 5,807,261 A | 9/1998 | Benaron |
| 5,987,346 A | 11/1999 | Benaron |
| 6,556,851 B1 * | 4/2003 | Ott et al. .......... 600/310 |
| 6,711,426 B2 * | 3/2004 | Benaron et al. .......... 600/342 |
| 7,264,616 B2 * | 9/2007 | Shehada et al. .......... 604/541 |
| 7,419,483 B2 * | 9/2008 | Shehada .......... 604/543 |
| 2002/0021866 A1 * | 2/2002 | Everett et al. .......... 385/31 |
| 2004/0254431 A1 * | 12/2004 | Necola Shehada .......... 600/327 |
| 2005/0203469 A1 * | 9/2005 | Bobroff et al. .......... 604/318 |

* cited by examiner

*Primary Examiner* — Tse Chen
*Assistant Examiner* — Rochelle Reardon (57) ABSTRACT

The present invention relates to fiberoptic sensors embedded within a surgical drain to monitor the condition of tissue proximate to the surgical drain and methods of processing data from the sensors. The light transmitting and collecting tips of the optical fibers are adapted to enable sideways interrogation of the adjacent tissues using optical techniques to measure the tissue condition. The light transmitting and collecting tips of the optical fibers may be bent at angle, disposed between a light absorbing and transmitting sheets, or uncladded to enable sideways emission and collection of light. Processing methods for reducing the site dependency of the measured data, maximizing the signal to noise ratio, and increasing the measurement sensitivity to changes in the tissue condition are described.

8 Claims, 9 Drawing Sheets

METHODS AND SENSORS FOR MONITORING INTERNAL TISSUE CONDITIONS

CROSS REFERENCE TO RELATED APPLICATIONS

This application claims the benefit of U.S. Provisional Application No. 60/652,939, filed Feb. 14, 2005, entitled Methods and Sensors for Monitoring Internal Tissue Conditions, the entire contents of which application are incorporated herein by reference.

FIELD OF THE INVENTION

The present invention relates to optical sensors embedded within a surgical drain to monitor the condition of organs and tissues proximate to the surgical drain and methods of processing data from the sensors.

BACKGROUND OF THE INVENTION

Monitoring of organ condition may be important after surgery such as organ transplantation and resection. Surgical complications, such as vascular complications, may disrupt adequate oxygen circulation to the tissue, which is critical to organ function and survival. Following liver surgery, for example, a physician may draw patient blood to determine the condition of the organ by measuring liver enzymes (such as transaminases) and clotting factors (such as prothrombin). Unfortunately, these blood tests reflect liver condition only at the time the blood sample is drawn, and changes in these laboratory values can often be detected only after significant organ damage has already occurred, permitting a limited opportunity for intervention by the physician to improve the condition of the organ or find a replacement organ in case of transplantation for the patient.

Other methodologies have been used to assess internal tissue conditions. For example, Doppler ultrasound techniques, angiography, implantable optical probes, and thermodilution catheters have been used to measure tissue oxygenation and/or perfusion. However, these techniques can be difficult to successfully apply to continuous monitoring of organ condition, and may provide only qualitative or indirect information regarding a condition, and/or may provide information about only a small segment of an organ.

Therefore, it is desirable to have a device and methods to aid physicians in predicting problems and complications associated with internal trauma or surgery. It is desirable to have a device which is positionable and removable with relatively minimal effort, minimally invasive and causes minimal discomfort for the patient, provides continuous current information about tissue or organ condition, provides direct information about tissue or organ condition, and/or provides feedback on the effects of interventions, such as medications or other procedures to improve tissue or organ. One convenient method for measuring the condition of internal tissues and organs is to embed optical reflectance sensors in a common surgical drain that is placed adjacent to the organ/tissue of interest during surgery.

Optical reflectance sensors involve the use of visible and/or near-infrared radiation to measure the absorbance of haemoglobin in a tissue bed to determine the oxygen saturation of hemoglobin. The optical absorption characteristics of the main oxygen carrier haemoglobin vary with its state of oxygenation. In general, an optical reflectance sensor illuminates the tissue with visible and/or near-infrared radiation and collects the reflected and/or backscattered light for spectral analysis to determine the state of tissue oxygenation. The oxygen saturation of hemoglobin can be estimated by measuring its optical absorption at predetermined wavelengths that allow the maximum distinction between oxyhemoglobin and deoxyhemoglobin. Certain reflectance sensors uses optical fibers to transmit the illumination light and collect the reflected light from the measurement location.

When such fiberoptic sensors are embedded in a surgical drain or in any other kind of probes to monitor adjacent tissues it may be required to adapt the tips or endings of such optical fibers to interrogate a tissue surface that is parallel to the axis of the optical fibers. This may be achieved by adjusting the tip of the optical fiber to allow the side-emission and/or side-collection of radiation to interrogate the adjacent tissues or organs. Micro mirrors and micro prisms may be fitted to the tip of the optical fibers to enable the side emission/collection of radiation to interrogate tissue, however, simpler and cheaper techniques are desired.

SUMMARY OF THE INVENTION

In one embodiment of the invention, the light transmitting and collecting tips of the optical fibers may have a sharp bend to enable side interrogation of the adjacent organs or tissues using optical reflectance/backscatter techniques.

In one embodiment of the invention, the light transmitting and collecting tips of the optical fibers may be disposed between an absorbing surface and a transparent sheath that is in contact with the tissue to enable side interrogation of the adjacent organs or tissues using optical reflectance/backscatter techniques.

In one embodiment of the invention, the portions of the sides of the light transmitting and collecting optical fibers may be processed to modify the cladding layer and allow the in and out leakage of light to enable side interrogation of the adjacent organs or tissues using optical reflectance/backscatter techniques.

These, as well as other objects, features and benefits will now become clear from a review of the following detailed description of illustrative embodiments and the accompanying drawings.

DETAILED DESCRIPTION OF ILLUSTRATIVE EMBODIMENTS

Figure 1:
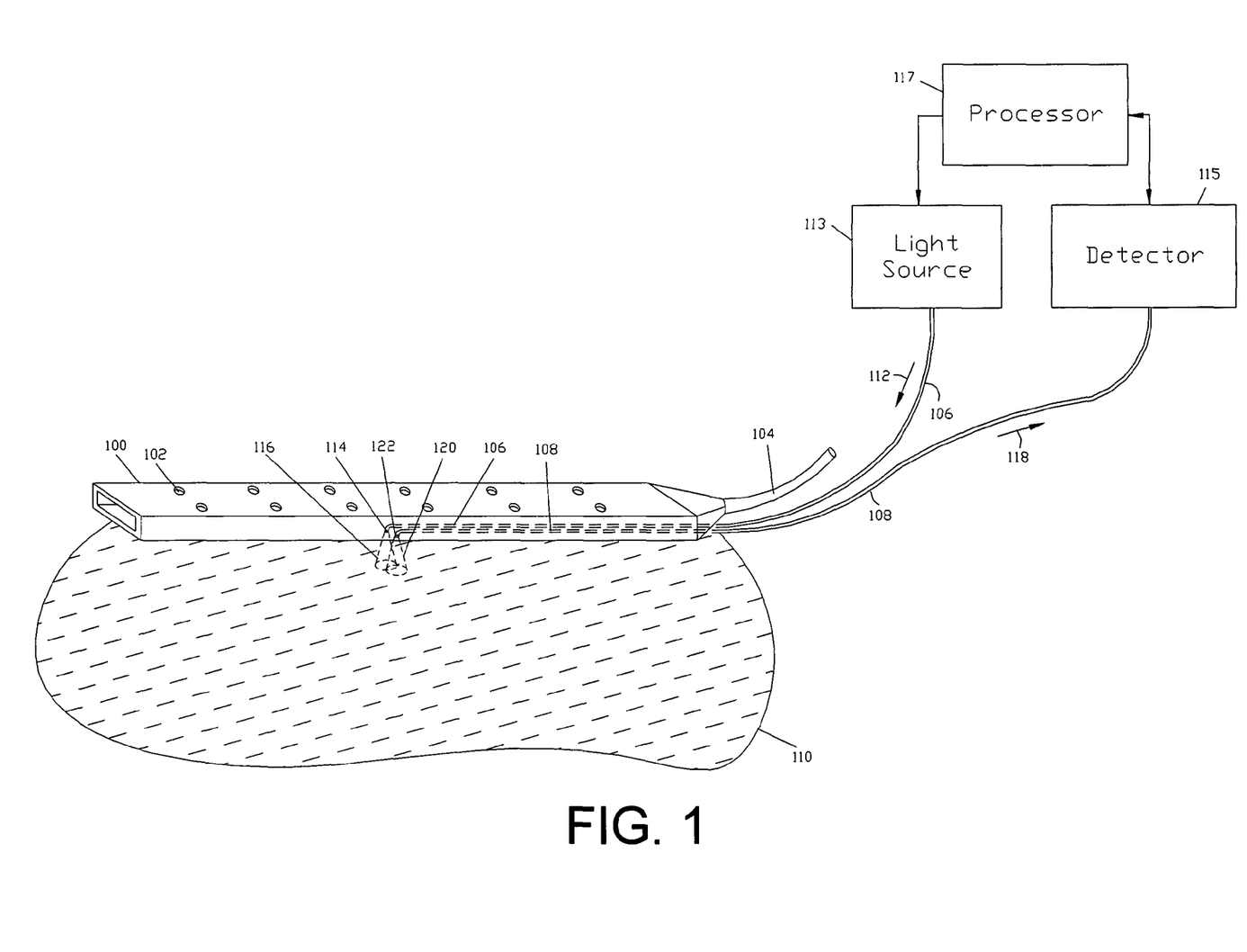
FIG. 1 shows a surgical drain with side-emitting fiberoptics to optically interrogate adjacent tissues.

Referring to FIG. 1, the present invention includes a surgical drain 100 with draining holes 102, a drainage collection tube 104, a first optical fiber 106, and a second optical fiber 108. The drain 100 is placed on the tissue 110 during surgery and the optical fibers 106 and 108 may be used to optically interrogate the tissue 110 to determine its condition.

The first optical fiber 106 may transmit the excitation radiation 112 that emerges from the distal aperture 114 of the optical fiber 106 to irradiate the cone of acceptance 116 within the tissue 110 and generate a returned radiation. The excitation radiation 112 may be generated by the light source 113. The light source 113 may be a lamp, a light emitting diode (LED), a combination of light emitting diodes of different wavelengths, or a laser. The excitation radiation 112 may be preferably in the visible wavelength band between 450 and 600-nm, however, it may be also in the ultraviolet, and/or infrared wavelength bands. A portion 118 of the returned radiation may enter the cone of acceptance 120 of the distal aperture 122 of the second optical fiber 108. The portion 118 of the returned radiation may be collected by the distal aperture 122 and guided through the second optical fiber 108 to a detector 115 that measures the spectral characteristics of the portion 118. The detector 115 may be a spectrometer, or one or more optically filtered light detectors. A processor 117 may analyze the spectral characteristics measured by the detector 115 to determine and display the condition of the tissue 110.

The present invention describes several configurations by which the tips of the optical fibers 106 and 108 may be adapted for the side emission and collection of radiation to interrogate the adjacent tissue 110. The fiberoptic tip configurations disclosed below may be used to interrogate biological tissue using optical reflectance/backscatter and/or induced-fluorescence spectroscopic techniques. Alternatively, these fiberoptic tip configurations may be readily modified for use in any other spectroscopic technique.

Figure 2A:
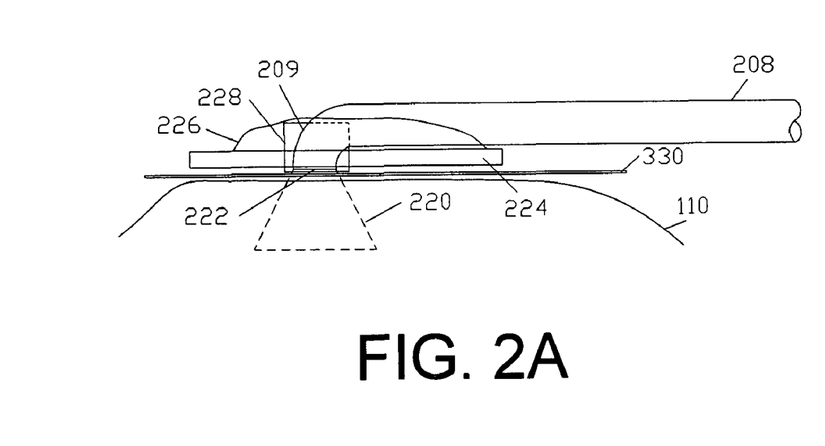
FIG. 2A shows a side-view of the bent-tip fiberoptic configuration.
Figure 2B:
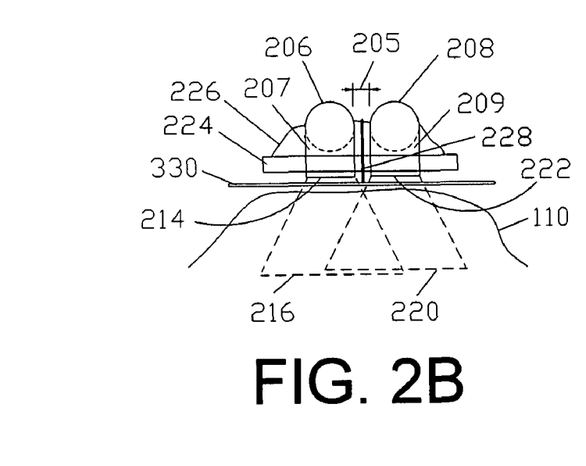
FIG. 2B shows a front-view of the bent-tip fiberoptic configuration.
Figure 2C:
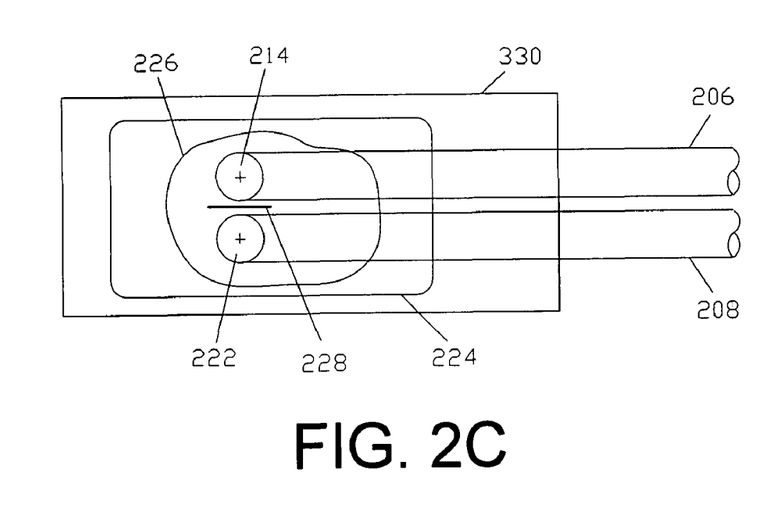
FIG. 2C shows a bottom-view of the bent-tip fiberoptic configuration.

The preferred fiberoptic tip embodiment using a bent-tip configuration is shown in FIG. 2A, FIG. 2B and FIG. 2C. In this configuration the optical fibers 206 and 208, preferably of the plastic type, have distal ends 207 and 209 that are fixated at a preselected distance 205 from each other and mechanically bent towards the tissue 110. The bend angle may be typically 90-degrees, however, it can be any other desired angle that would allow the cones of acceptance 216 and 220 of intersecting with the adjacent tissue 110. The distal ends 207 and 209 may be bent to have the same or different bend angles. The distal ends 207 and 209 may be fixated directly to each other or to a support structure 224, for example, plastic sheet, using a bonding material 226 such as, for example, epoxy. Portions of the distal ends 207 and 209 may be re-cladded with a cladding material and/or painted with a reflective material to minimize the loss of light through to the sharp bend in the optical fiber.

The distal apertures 214 and 222 of the optical fibers 206 and 208 may have cones of acceptance 216 and 220, respectively, that may or may not be intersecting with each other. In an optical fiber the cone of acceptance is an imaginary cone within which optical power is coupled into the guided rays of an optical fiber. An optical isolator 228 may be placed between the bent distal ends 207 and 209 of the optical fibers 206 and 208 to prevent crosstalk between their corresponding apertures 214 and 222. The optical isolator 228 may be an opaque absorptive sheet. Alternatively, the optical isolator 228 may be replaced by an absorptive paint applied over the sides of the tip of the optical fiber. A thin sheet 330 of transparent material such as medical grade silicone may be used to cover the apertures 214 and 222 of the optical fibers 206 and 208 to isolate them from adjacent tissue 110.

Figure 3A:
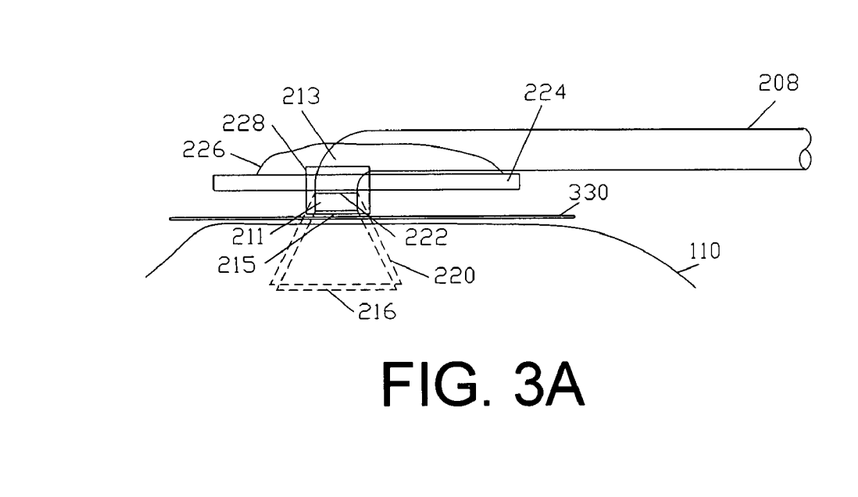
FIG. 3A shows a side-view of the bent-tip fiberoptic configuration with unequal tip lengths.
Figure 3B:
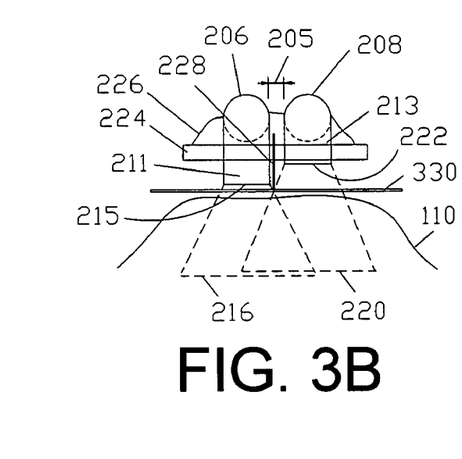
FIG. 3B shows a front-view of the bent-tip fiberoptic configuration unequal tip lengths.
Figure 3C:
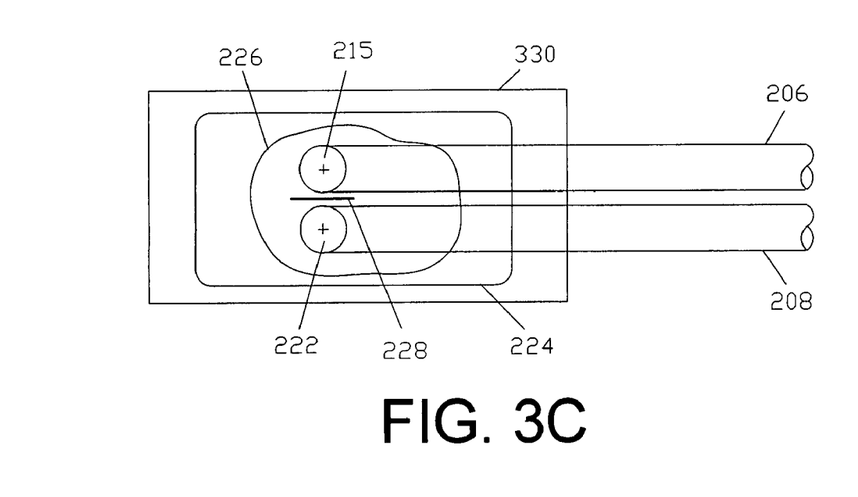
FIG. 3C shows a bottom-view of the bent-tip fiberoptic configuration unequal tip lengths.

An alternative bent-tip configuration is shown in FIG. 3A, FIG. 3B and FIG. 3C where the bent distal ends 211 and 213 of the optical fibers 206 and 208 are unequal in length, respectively. In this example, the bent fiber tip 211 of the optical fiber 206 is longer than the bent fiber end 213 of the optical fiber and 208. This configuration may be advantageous in minimizing crosstalk between the apertures 215 and 222.

Figure 4A:
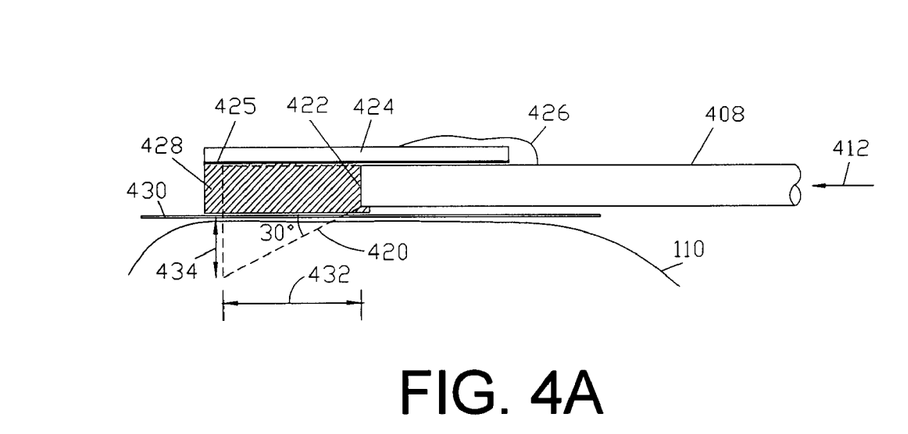
FIG. 4A shows a side-view of the straight-tip fiberoptic configuration.
Figure 4B:
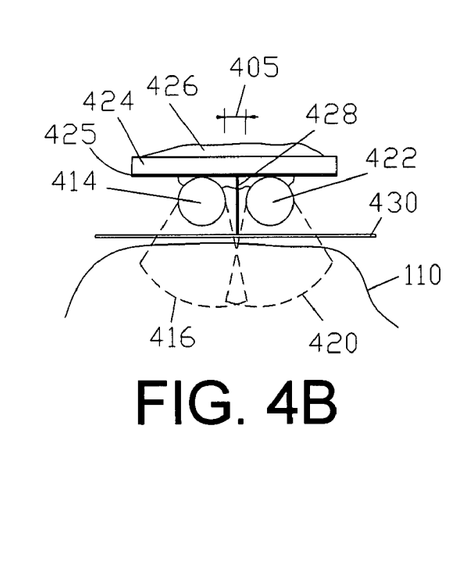
FIG. 4B shows a front-view of the straight-tip fiberoptic configuration.
Figure 4C:
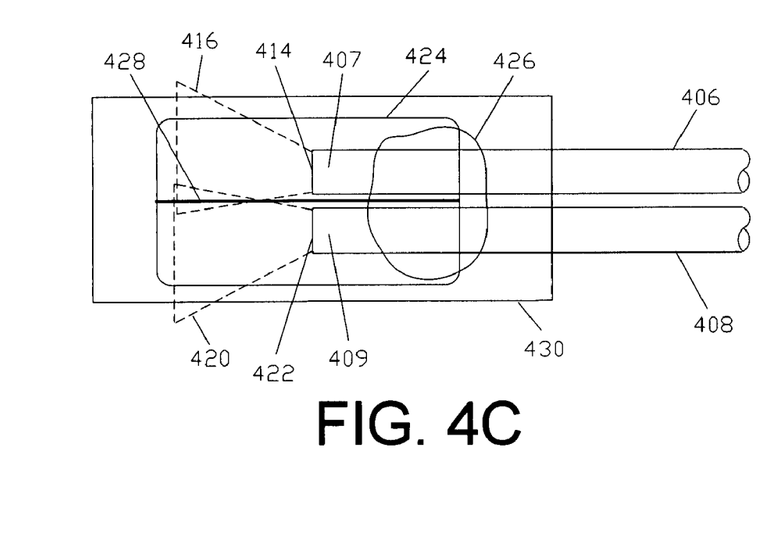
FIG. 4C shows a bottom-view of the straight-tip fiberoptic configuration.

An alternative fiberoptic tip embodiment using a straight tip configuration is shown in FIG. 4A, FIG. 4B and FIG. 4C. In this configuration, the distal ends 407 and 409 of the optical fibers 406 and 408 are kept straight and may be fixated to a support structure 424, for example a plastic sheet, using a bonding material 426 such as, for example epoxy. The distal ends 407 and 409 of the optical fibers 406 and 408 are fixated at a preselected distance 405 from each other and are sandwiched between an optically absorptive layer 425 and an optically transparent sheet 430. The absorptive layer 425 may be a matt black plastic sheet or a coating applied to a portion of the support structure 424. The transparent sheet 430 may be a thin (e.g. 0.005") medical grade silicon sheet or a plastic sheet that separates the distal ends 407 and 409 from the underlying tissue 110.

An optical isolator 428 may be placed between the distal ends 407 and 409 to isolate the cones of acceptance 416 and 420 to prevent crosstalk between their corresponding apertures 414 and 422. The optical isolator 428 may be an optically opaque plastic sheet. Any radiation hitting the absorptive layer 425 and the optical isolator 428 gets absorbed and may not be collected by the receiving aperture. This configuration will ensure that most of the returned radiation is collected from the tissue 110 through the transparent sheet 430 rather than being a direct transmission between the apertures 414 and 422. Making one distal fiber tip slightly longer than the other such that the apertures 414 and 422 are not adjacent may further minimize crosstalk between the fibers 406 and 408.

The optical fibers 406 and 408 may have cones of acceptance 416 and 420 that are large enough to penetrate the adjacent tissue 110 even with the apertures 414 and 422 being nearly perpendicular to the surface of the tissue 110 as shown in FIG. 4A. Some plastic optical fibers may have an approximately 60-degree angle of acceptance and may be suitable for use in this configuration. For such fibers, the penetration depth 434 into the tissue 110 is about 0.6 times ($\approx \tan(30°)$) the height 432 of the cone of acceptance 420.

In one operational mode, for example, the excitation radiation 412 transmitted through the optical fiber 408 emerges from its aperture 422 into the cone of acceptance 420 as shown in FIG. 4A. The upper portion of the cone of acceptance 420 may be absorbed by the absorptive layer 425 and the optical isolator 428 while the lower portion of the cone of acceptance 420 passes through the transparent sheet 430 and into the underlying tissue 110 to produce a returned radiation. The returned radiation may be scattered and/or reflected back into the cone of acceptance 416 of the adjacent optical fiber 406 that collects the returned radiation and transmits it back to a detector 115 for spectral measurement to determine the condition of the tissue 110. The excitation radiation 412 used to interrogate the tissue may preferably be in the visible spectral band, however it can include light in ultraviolet and/or the infrared spectral bands as well.

Figure 5A:
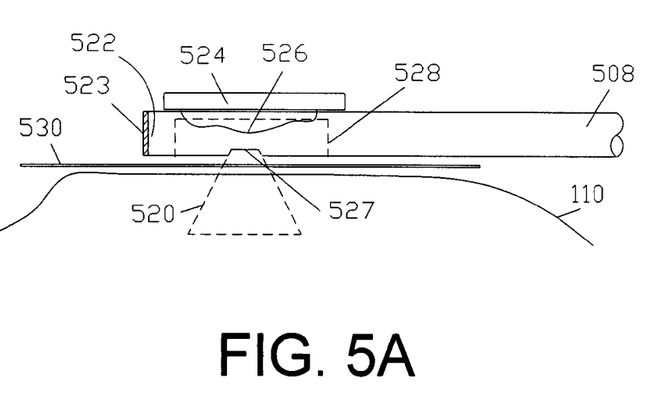
FIG. 5A shows a side-view of the side-leak fiberoptic configuration with a point aperture.
Figure 5B:
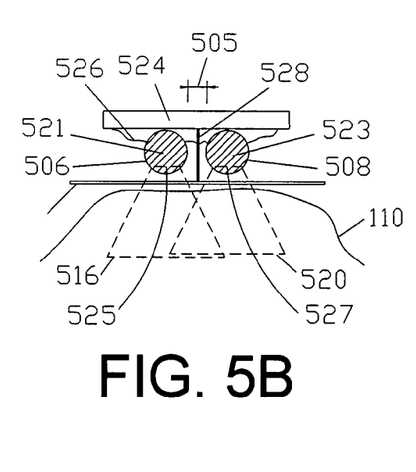
FIG. 5B shows a front-view of the side-leak fiberoptic configuration with a point aperture.
Figure 5C:
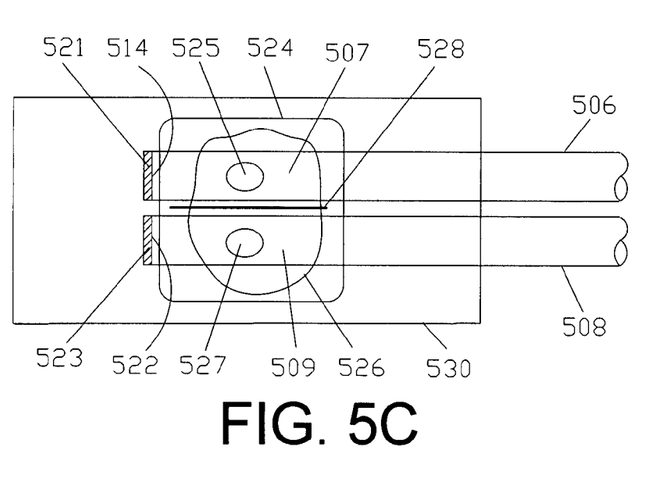
FIG. 5C shows a bottom-view of the side-leak fiberoptic configuration with a point aperture.

An alternative fiberoptic tip embodiment using a side-leaking tip configuration is shown in FIG. 5A, FIG. 5B and FIG. 5C. In this configuration, the distal ends 507 and 509 of the optical fibers 506 and 508 are kept straight and fixated at a preselected distance 505 from each other. The optical fibers 506 and 508 may be of the plastic type, however, they may also be of the glass or quartz type.

The end apertures 514 and 522 of the optical fibers 506 and 508 are covered or coated with a reflective material 521 and 523 to reflect light back into the fiber and prevent its loss through the apertures 514 and 522. The cladding layer may be removed from a side portion of the distal ends 507 and 509 of the optical fibers 506 and 508 to create the side-apertures 525 and 527 that may leak the light out of or into the fibers. The cladding layer may be removed chemically, thermally or mechanically. The cladding of the fiber may be removed at a single point on the wall of the fiber as shown in FIG. 5 or along a line on the wall of the fiber (not shown) such that the fiber would leak or collect light along a segment of its length. An optical isolator 528 may be placed between the side-apertures 525 and 527 to isolate their cones of acceptance 516 and 520 and minimize crosstalk. The optical isolator 528 may be an opaque absorptive sheet. A thin sheet 530 (e.g. 0.005") of transparent material such as medical grade silicone may be used to cover the apertures 525 and 527 of the optical fibers 506 and 508 to isolate them from adjacent tissue 110.

Figure 6A:
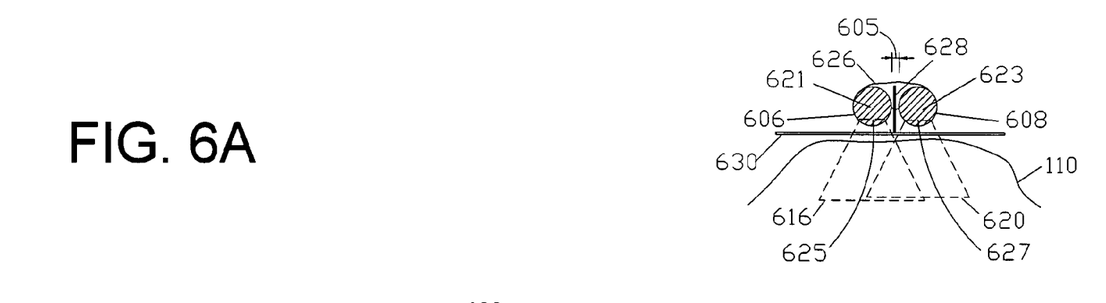
FIG. 6A shows a side-view of the side-leak fiberoptic configuration with a line aperture.
Figure 6B:
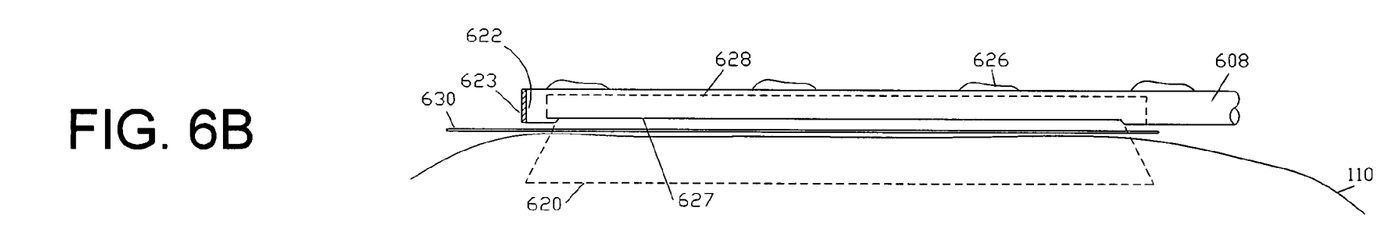
FIG. 6B shows a front-view of the side-leak fiberoptic configuration with a line aperture.
Figure 6C:
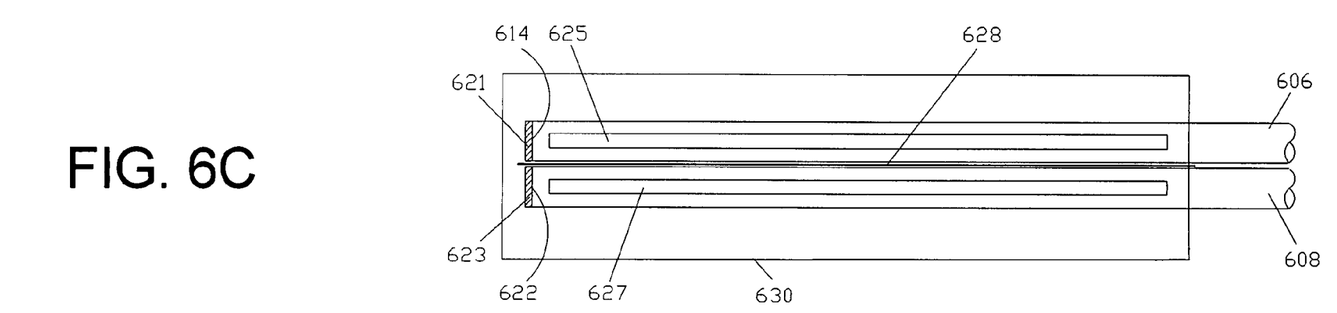
FIG. 6C shows a bottom-view of the side-leak fiberoptic configuration with a line aperture.

In an alternative embodiment shown in FIG. 6A, FIG. 6B and FIG. 6C, the cladding layer may be removed from a line portion along a side of the fibers 606 and 608 to create line-apertures 625 and 627 that may leak light out of or into the corresponding fibers. The optical fibers 606 and 608, preferably of the plastic type, may be fixated to each other with the optical isolator 628 placed in-between. The optical isolator 628 may be an opaque absorptive flexible material that is placed between the fibers 606 and 608 to separate their adjacent line-apertures 625 and 627 to isolate the wedges of acceptance 616 and 620 and minimize crosstalk between their corresponding line-apertures 625 and 627. The end apertures 614 and 622 of the optical fibers 606 and 608 are covered or coated by a reflective material 621 and 623 to reflect light back into the fiber and prevent its loss. A thin sheet 630 of transparent material such as medical grade silicone may be used to cover the line-apertures 625 and 627 of the optical fibers 606 and 608 to isolate them from adjacent tissue 110. One advantage of the above embodiment is that it may allow the optical interrogation of a long segment of the tissue 110 rather than just a single point. This will produce a spatially averaged measurement and decrease the site-dependency of the spectral measurement.

Figure 7A:
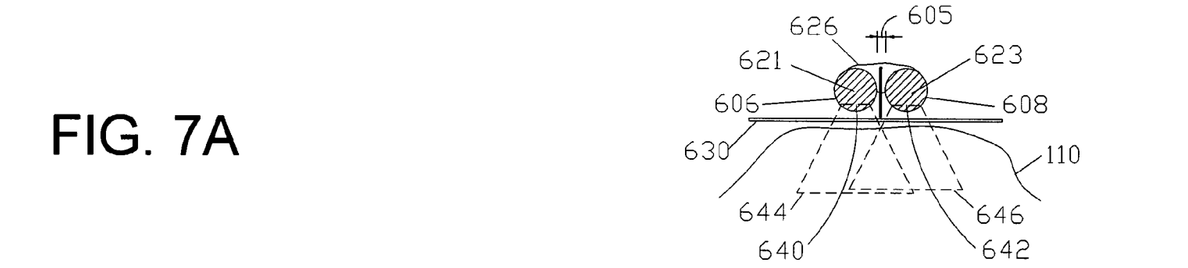
FIG. 7A shows a side-view of the side-leak fiberoptic configuration with a series of apertures.
Figure 7B:
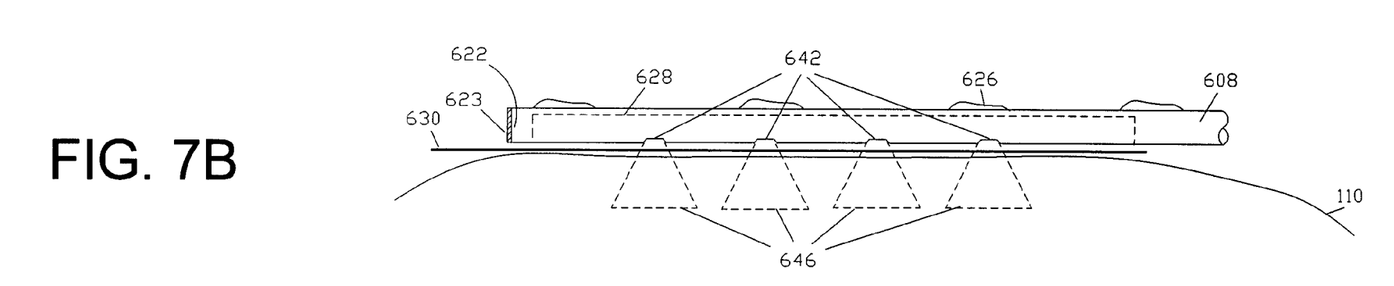
FIG. 7B shows a front-view of the side-leak fiberoptic configuration with a series of apertures.
Figure 7C:
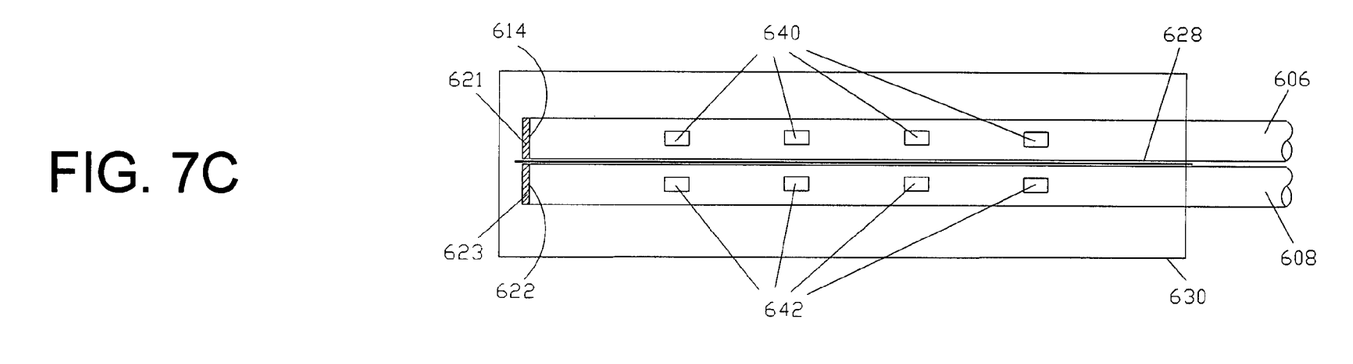
FIG. 7C shows a bottom-view of the side-leak fiberoptic configuration with a series of apertures.

In another alternative embodiment shown in FIG. 7A, FIG. 7B and FIG. 7C, the cladding layer may be removed from multiple consecutive portions along a side of the fibers 606 and 608 to create a series of point-aperture 640 and 642 that may leak light out of or into the corresponding fibers. The optical fibers 606 and 608, preferably of the plastic type, are fixated to each other with the optical isolator 628 placed in-between. The optical isolator 628 may be an opaque absorptive flexible material that is placed between the fibers 606 and 608 to separate their adjacent series of point-aperture 640 and 642 to isolate their cones of acceptance series 644 and 646 and minimize crosstalk between their corresponding fibers 606 and 608. The end apertures 614 and 622 of the optical fibers 606 and 608 are covered or coated by a reflective material 621 and 623 to reflect light back into the fiber and prevent its loss. A thin sheet 630 of transparent material such as medical grade silicone may be used to cover the line-apertures 640 and 642 of the optical fibers 606 and 608 to isolate them from adjacent tissue 110. One advantage of the above embodiment is that it may allow the optical interrogation of a long segment of the tissue 110 rather than just a single point. This will decrease the site-dependency of the spectral measurement.

Measurement acquired from different sites of the same tissue may be slightly different due to tissue inhomogeneities such as, for example, scars and/or variations in the local microcirculation. This factor is known as the site-dependency of the measurement and may introduce variability in the measured parameter if the surgical drain with its embedded sensors moves relative to the tissue. As a result of respiration, heart pulsation, peristalsis, muscular contraction and/or patient movement, the surgical drain may slightly slide on the surface of the tissue or organ on which it is placed. This sliding movement may change the tissue site being interrogated by a given sensor embedded within the surgical drain and therefore the sensor may produce variable measurements of the tissue condition if the tissue being interrogated was inhomogeneous. Site-dependent variations may be reduced by synchronizing the tissue measurement to a particular phase of the motion cycle as describe below.

Figure 8:
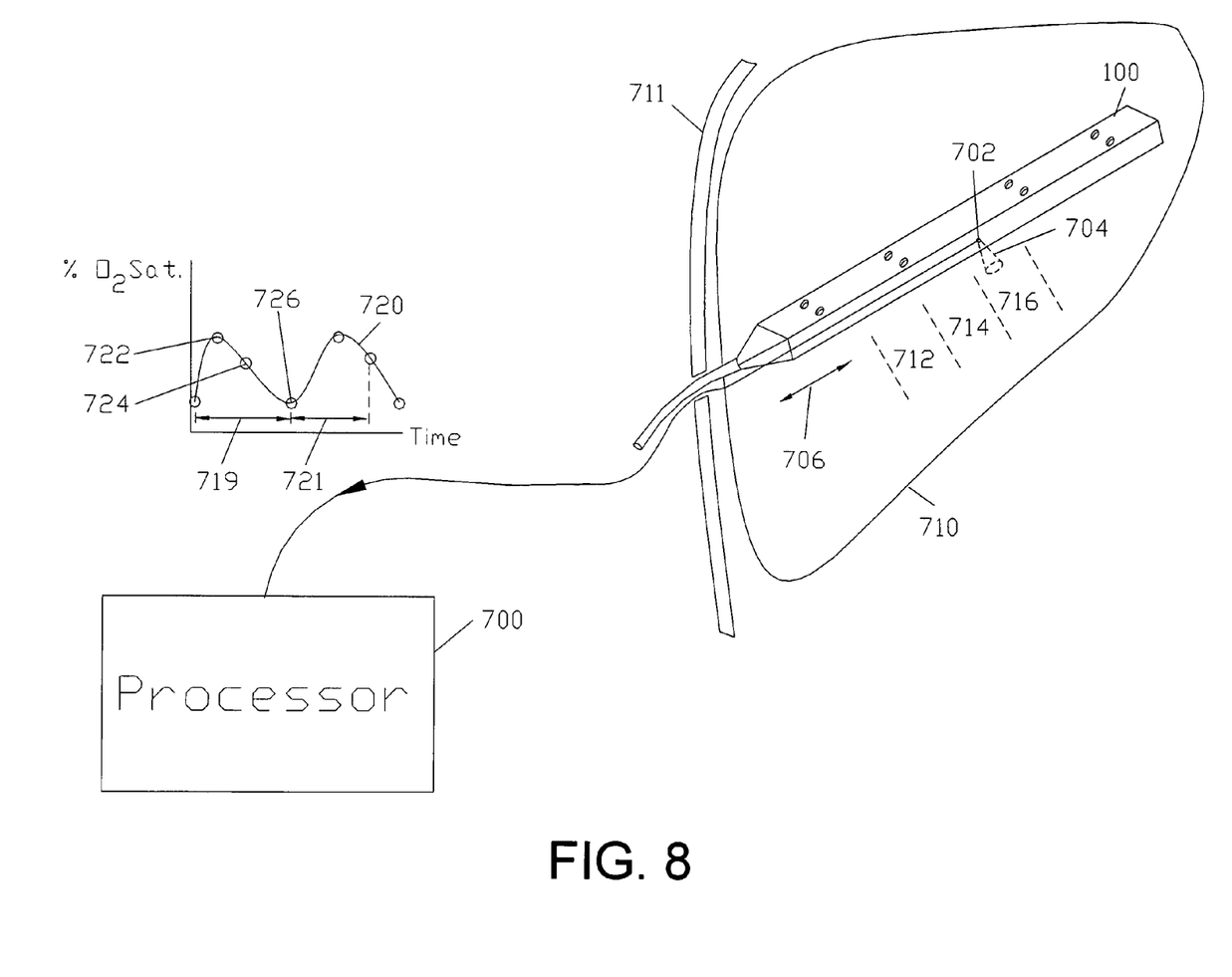
FIG. 8 shows a method to minimize the motion-related measurement variation.

For example, the movement of the abdominal diaphragm during respiration may lead to a sliding motion 706 of the surgical drain 100 over an abdominal organ 710 such as the liver as shown in FIG. 8. During this motion, the probing beam 704 of the oxygen saturation sensor 702 may interrogate different tissue sites 712, 714, and 716 and the sensor 702 may measure different oxygen saturation values 722, 724, and 726, respectively, of the same organ 710. The tissue sites 712, 714, and 716 may have, for example, 100, 95 and 90% oxygen saturation due to differences in their local microcirculation and hence perfusion. Therefore the measured oxygen saturation value may vary depending on the position of the sensor 702 relative to the tissue sites 712, 714, and 716 when the measurement is acquired. This motion-related measurement variability may be periodic in nature as shown by the waveform 720 in FIG. 8. The processor 700 may determine the period 719 of the waveform 720 by for example analyzing the time between two peaks, troughs, or zero crossings. Subsequently, the processor 700 may select and record the oxygen saturation value recorded at a peak 722, a trough 726, or a specific phase 721 of the waveform 720. For example, if processor always selects the oxygenation value recorded at phase 721 from the beginning of the cycle, then the selected oxygenation value would be most likely measured from the corresponding site 714 of the tissue 710. Alternatively, the processor 700 may simply select, for example, the minimum 726, the maximum 722 or the median of the oxygenation values. Alternatively, the processor 700 may simply take an average of all measurements acquired throughout a given variation cycle 720 and display the mean value as that representing the average oxygenation of the organ 710. Although the example above describes a method for reducing the site dependency of oxygen saturation measurement, the method is applicable to any other parameter including tissue perfusion, pH, material concentration, biochemical composition, and haemoglobin concentration.

The returned radiation collected by any of the fiberoptic configurations described above may be spectrally analyzed using a detector such as a spectrometer. The integration time of the spectrometer may be fixed and is usually selected to produce an unsaturated spectrum (i.e. does not exceed the dynamic range of the detector) within the range of expected return radiation intensities. A constant integration time may be a limiting factor if the measured light intensities are relatively low because the measured radiation signal may become comparable to the noise levels of the detector. In addition, the low intensity radiation signal would be measured over only a fraction of the detector's dynamic range.

A simple algorithm may be used to dynamically vary the integration time of the spectrometer based on the intensity of the returned radiation. This may provide an improved signal to noise ratio and that the dynamic range of the detector may be utilized to its maximum. The dynamic integration time protocol works as follows:
1. Predetermine the maximum Intensity Counts $I_{max}$ of the spectrometer.
2. Start with an integration time set to a relatively short duration $T_1$ that would guarantee that any radiation intensity, within the range of interest, would produce an unsaturated spectrum (i.e. $\leq I_{max}$).
3. Using $T_1$ as integration time, acquire a spectrum $S_1$.
4. Determine the maximum intensity $I_1$ of the spectral band of interest within $S_1$.
5. Assuming a linear relation between the integration time and intensity, calculate a new Integration time $T_2 = T_1 (I_{max}/I_1)$.
6. Use the T2 to acquire the new spectrum $S_2$ for analysis.
7. $S_2$ may have a maximum intensity $I_2$ that is closer in value to $I_{max}$.

The above loop may be iteratively repeated several times to refine the $T_2$ selection and overcome any nonlinearities that may be present in the integration time versus intensity relationship.

The surgical drain 100 may include fiberoptics to optically interrogate the adjacent tissue 110 as shown in FIG. 1. The drain 100 is placed on the tissue 110 during surgery and the optical fibers 106 and 108 may be used to measure physical, physiological or biochemical parameters of the underlying tissue during the first few days following surgery. These measured parameters may be compared to their normal values in healthy tissue. However, in many cases it may be valuable to detect changes in the tissue condition relative to a previously measured condition of the same tissue when the tissue was known to be healthy, rather than to compare the tissue condition to an absolute measurement. Relative comparison of successive spectroscopic data acquired from the same organ or tissue may be advantageous for detecting changes in the tissue condition and the stability of a known healthy condition. For example, a first spectroscopic measurement of a newly transplanted liver may be acquired immediately following transplantation when the surgeons have just confirmed that the liver is functioning properly and that the hepatic tissue is healthy. The drain 100 may acquire successive spectroscopic measurements throughout the postoperative monitoring period and a processor may compare the successive spectroscopic measurements to the first spectroscopic measurement and detect any deviations. Comparing the first spectrum to successive spectra may be achieved using a simple spectral matching technique (e.g. correlation coefficient, sum of absolute differences, etc.), a statistical pattern matching method, statistical parameters (e.g. percentiles, skewness, kurtosis, etc.), neural networking, or mathematical modeling. The processor may display a stability index, a correlation coefficient, or percentage indicating the mismatch in the spectral profile of each newly acquired spectrum in comparison to the first acquired spectrum that was acquired when it was known that the tissue is healthy. This display of tissue stability may be useful in alarming the surgeons to changes in the tissue condition.

Figure 9A:
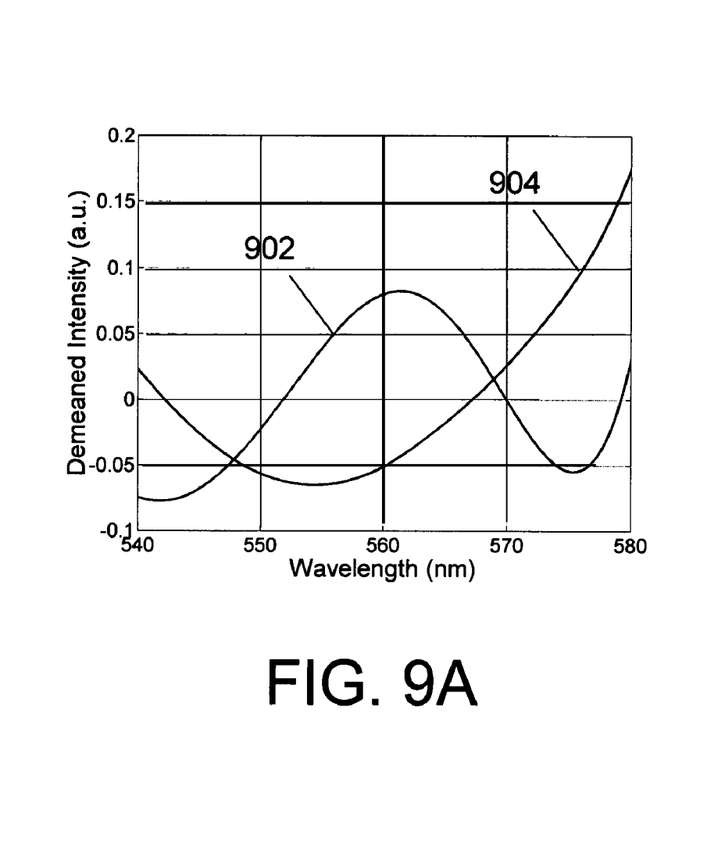
FIG. 9A shows typical reflectance spectra of pig liver under different blood perfusion conditions.
Figure 9B:
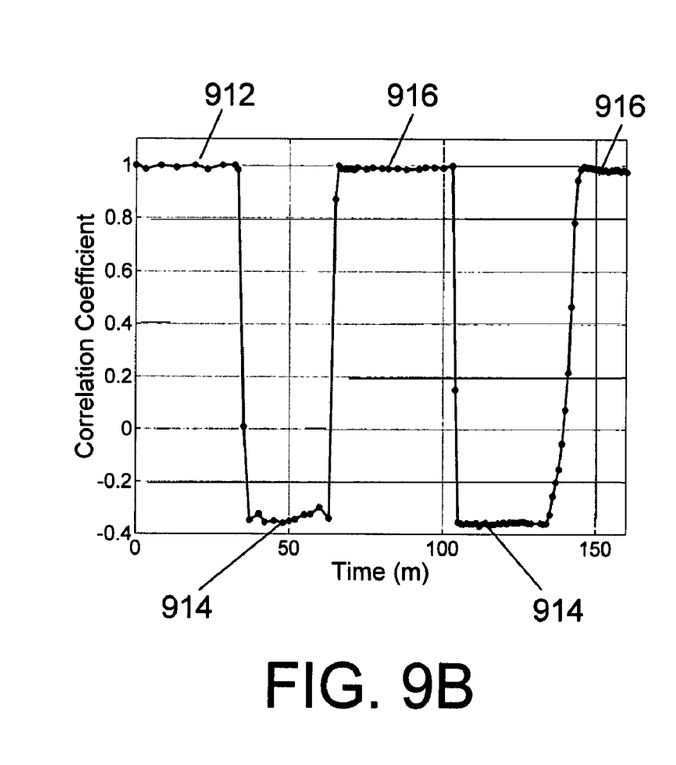
FIG. 9B shows spectral correlation between a first spectrum and subsequent reflectance spectra measured from the liver under different blood perfusion conditions.

The advantage of this data processing method in detecting changes in tissue oxygenation or perfusion is illustrated in FIG. 9A and FIG. 9B. A pig model was used to simulate the clinical scenario of hepatic artery thrombosis (HAT) and the surgical removal of the thrombosis to reestablish normal blood flow (i.e. reperfusion). FIG. 9A shows the reflectance spectra of visible light (540-580 nm) from the surface of the pig liver under normal and reduced blood perfusion. The reflectance spectrum 902 is obtained from the surface of the liver under normal perfusion conditions. On the other hand, the reflectance spectrum 904 is obtained from the surface of the liver while the hepatic artery is occluded to simulate HAT. The hepatic artery is the main source of oxygenated blood to the liver and by its occlusion the hepatic tissue becomes deoxygenated. FIG. 9B shows a time trace of the correlation coefficient between the first reflectance spectrum (measured at time zero) from the normally perfused liver and successive reflectance spectra (measured at subsequent times) from the liver under normal perfusion 912, HAT 914, and reperfusion 916 conditions. As illustrated in the above example, this data processing method appears to be capable of the accurate and rapid detection of changes in tissue perfusion and oxygenation. Although the above example illustrates its application in detecting changes in tissue perfusion, the method may be applied to detect any other condition that alters the optical characteristics of the tissue such as, for example, tissue rejection, bile concentration, haemoglobin concentration, biochemical composition, necrosis, and edema. The method may be made more sensitive to certain tissue changes than others by selecting specific wavelength bands for the spectral comparison analysis. For example, comparing spectra in the 540 to 580-nm wavelength band may be more indicative of changes in perfusion and oxygenation, while comparing spectra in the 450-470-nm wavelength band may be more indicative of changes in the bile concentration within the tissue.

Although the above detailed description describes and illustrates various preferred embodiments, the invention is not so limited. Many modifications and variations will now occur to persons skilled in the art. As such, the preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Accordingly, the foregoing description should not be read as pertaining only to the precise structures described and illustrated in the accompanying drawings, but rather should be read consistent with and as support to the following claims, which are to have their fullest and fair scope.

What is claimed is:

1. A probe for sensing a tissue condition comprising:
a surgical drain with a plurality of draining holes and a drainage collection tube;
a first optical fiber with a distal tip to transmit light to the tissue;
a second optical fiber with a distal tip to receive returned light from the tissue;
wherein the distal tips of the first and the second optical fibers are:
i) disposed behind a light transmitting surface,
ii) bent towards the light transmitting surface, and
iii) unequal in length after the said bend, wherein;
the light transmitting surface is in contact with the tissue.

2. The probe of claim 1, wherein the tissue condition sensed by the probe is selected from the group: percent oxygen saturation, oxygenation, perfusion, pH, biochemical composition, haemoglobin concentration, bile concentration, and drug concentration.

3. A probe for sensing a tissue condition comprising:
a surgical drain with a plurality of draining holes and a drainage collection tube;
a first optical fiber having a distal segment to emit light on the tissue, wherein all but a side portion of the distal segment of the first optical fiber is cladded;
a second optical fiber having a distal segment to collect returned light from the tissue, wherein all but a side portion of the distal segment of the second optical fiber is cladded;
the distal segment of the first optical fiber and the distal segment of the second optical fiber are optically insulated from each other;
wherein the distal tips of the first and the second optical fibers are:
i) disposed behind a light transmitting surface,
ii) bent towards the light transmitting surface, and
iii) unequal in length after the said bend, wherein the light transmitting surface is in contact with the tissue.

4. The probe of claim 3, wherein the side portion is a continuous line along the distal segment.

5. The probe of claim 3, wherein the tissue condition sensed by the probe is selected from the group: percent oxygen saturation, oxygenation, perfusion, pH, biochemical composition, haemoglobin concentration, bile concentration, and drug concentration.

6. A probe for sensing a tissue condition comprising:
a surgical drain with a plurality of draining holes and a drainage collection tube;
a first optical fiber with a distal tip that is bent at a first angle to transmit light to the tissue;
a second optical fiber with a distal tip that is bent at a second angle to receive returned light from the tissue;
wherein the distal tips of the first and the second optical fibers are:
i) optically insulated from each other,
ii) disposed behind a light transmitting surface, wherein the light transmitting surface is in contact with the tissue, and
iii) bent towards the light transmitting surface, wherein the first and second bend angles are different.

7. The probe of claim 5, wherein the distal tip of the first optical fiber and the distal tip of the second optical fiber are of unequal lengths after the bent.

8. The probe of claim 5, wherein the tissue condition sensed by the probe is selected from the group: percent oxygen saturation, oxygenation, perfusion, pH, biochemical composition, haemoglobin concentration, bile concentration, and drug concentration.

* * * * *